United States Patent
Gauché et al.

(10) Patent No.: US 8,277,519 B2
(45) Date of Patent: Oct. 2, 2012

(54) HAIR TREATMENT METHODS

(75) Inventors: Céline Gauché, Fleet (GB); Jamie Anthony Hawkes, Leeds (GB); David Malcolm Lewis, Otley (GB)

(73) Assignee: Perachem Limited, Leeds, Yorkshire (GB)

( * ) Notice: Subject to any disclaimer, the term of this patent is extended or adjusted under 35 U.S.C. 154(b) by 0 days.

(21) Appl. No.: 13/119,188

(22) PCT Filed: Sep. 10, 2009

(86) PCT No.: PCT/GB2009/051162
§ 371 (c)(1),
(2), (4) Date: Apr. 21, 2011

(87) PCT Pub. No.: WO2010/032034
PCT Pub. Date: Mar. 25, 2010

(65) Prior Publication Data
US 2011/0189116 A1    Aug. 4, 2011

(30) Foreign Application Priority Data

Sep. 16, 2008 (GB) .................................. 0816943.5
Oct. 16, 2008 (GB) .................................. 0818975.5

(51) Int. Cl.
*A61Q 5/10* (2006.01)
(52) U.S. Cl. ......... 8/405; 8/435; 8/455; 8/587; 132/202; 132/208

(58) Field of Classification Search .............. 8/405, 435, 8/587, 455; 132/202, 208
See application file for complete search history.

(56) References Cited

U.S. PATENT DOCUMENTS

| | | | |
|---|---|---|---|
| 3,213,129 A | 10/1965 | Berth et al. | |
| 4,054,413 A | 10/1977 | Feinland et al. | |
| 4,946,472 A | 8/1990 | Motono | |
| 5,104,413 A | 4/1992 | Ikeda | |
| 2006/0096042 A1* | 5/2006 | Schonert et al. | 8/406 |

FOREIGN PATENT DOCUMENTS

| | | |
|---|---|---|
| FR | 1011151 A | 6/1952 |
| GB | 721831 | 1/1955 |
| GB | 926977 | 5/1963 |
| GB | 1077758 | 8/1967 |
| GB | 1334636 | 10/1973 |

OTHER PUBLICATIONS

Patent Cooperation Treaty, PCT International Search Report and Written Opinion of the International Searching Authority for Application No. PCT/GB2009/051162 dated May 21, 2010, 16 pages.

* cited by examiner

*Primary Examiner* — Eisa Elhilo
(74) *Attorney, Agent, or Firm* — Stephen F. Swinton, Jr.; Hoffman Warnick LLC

(57) ABSTRACT

A method of colouring a material, the method comprising the steps of: a)applying to the material a composition comprising a sulphur-containing nucleophile; and b)applying to the material a composition comprising a dye compound selected from a dye class other than the class of reactive dyes.

7 Claims, No Drawings

HAIR TREATMENT METHODS

The present invention relates to methods for colouring materials, in particular colouring keratinous fibre materials, for example hair.

The colouring of human hair is a long-established practice in many cultures. There are many challenges for those working in the field of hair colouration. It is desirable to provide dyes and dyeing methods by which hair can be predictably coloured to consistently provide the desired shade. Hair colouring methods should be efficient in order to allow short contact times which provide wash durable and light durable colour and any damage to the hair should be kept to a minimum.

It is desirable to offer a user a wide range of colours for use in hair colouration. It would also be highly desirable to provide a hair colour which is durable to normal washing of the hair but which can be easily removed from the hair if desired. Current methods of removing artificial colour from the hair involve oxidatively bleaching the dyed hair which causes damage to the hair and does not usually return the hair to its original pre-dyed colour.

Permanent hair colouring compositions of the prior art have typically included colourless dye precursor compounds which react in situ via an oxidative coupling mechanism to form the coloured species. One problem with such compositions is that the colour may continue to develop for several hours or days after application and thus it may be difficult to predictably achieve the desired colour. It is also known to use reactive dye compounds in permanent hair colouring compositions.

The colour chemist is also aware of many other dye classes which offer a wide variety of different colours. However many previous attempts to colour hair using these different classes of dye have been unsuccessful due to poor wash fastness and poor build up of the colour produced. It is known to use some pre-formed chromophores available in the textile industry as semi-permanent hair dyes. However such compounds have not previously been successfully used to permanently dye human hair.

It is an aim of the present invention to provide alternative hair dye compositions and methods, in particular for use in permanent dyeing of human hair.

According to a first aspect of the present invention there is provided a method of colouring a material, the method comprising the steps of:
a) applying to the material a composition comprising a sulphur-containing nucleophile; and
b) applying to the material a composition comprising a dye compound selected from a dye class other than the class of reactive dyes.

The term "reactive dyes" is used to define a particular class of dyes and would be readily understood by the person skilled in the art of colour science. A reactive dye typically contains an electrophilic group that can be activated and allowed to directly react with a nucleophile in the substrate, forming a covalent bond. Reactive dye compounds may typically include a vinyl sulfone, an acrylamido or a halogenated triazine moiety, but the skilled person would be aware of dyes of other structures falling within this class.

In step (b) of the method of the present invention a dye compound is applied to the material. By the term "dye compound" we mean to refer to a compound in which the chromophore is fully formed. Thus the dye compounds of the present invention are distinct from the dye precursor compounds of the prior art which are oxidised upon application to the hair to provide the desired colour in situ. Suitably the dye compound of the present invention does not itself undergo a colour change upon or following application to the material.

Preferably the material treated in the method of the present invention is a keratinous material.

More preferably it is a keratinous fibre material, although the method of the present invention may also be used to dye non-fibrous keratinous based material, for example finger or toe nails. Most preferably the method of the present invention is a method of dyeing hair, in particular human hair.

Steps a) and b) may be carried out sequentially or they may be carried out simultaneously. Thus in some embodiments the method of the present invention comprises applying to the hair a first composition comprising a sulphur-containing nucleophile and then applying to the material a second composition comprising a dye compound. Alternatively a composition comprising a dye compound may be applied to the hair first, followed by a composition comprising a sulphur-containing nucleophile.

In preferred embodiments steps a) and b) are carried out simultaneously and the method of the present invention comprises applying to the material a single composition comprising both a dye compound as defined herein and a sulphur-containing nucleophile, hereinafter referred to as "the colouring composition".

According to a second aspect of the present invention there is provided a colouring composition comprising a sulphur-containing nucleophile and a dye compound selected from a dye class other than the class of reactive dyes.

Any suitable sulfur-containing nucleophile may be used. Preferred sulfur-containing nucleophiles include thiols and sulfite containing species.

Suitable thiols for use in the present invention include thioglycolic acid, thiolactic acid, dihydrolipoate, thioglycerol, mercaptopropionic acid, cysteine, N-substituted cysteines, cysteamines, N-substituted cysteamines, thioethanol, thiosulfate and 1-thiopropane 3-sulfonate. Thioglycolic acid is especially preferred.

Suitable sulfite containing species include hydrosulfite, bisulfite and sulfite salts. Alkali metal sulfite salts are preferred, especially sodium sulfite.

Preferably the colouring composition comprises at least 0.1 wt % of one or more sulphur-containing nucleophiles, preferably at least 0.5 wt %, more preferably at least 1 wt %, more preferably at least 2 wt %. The colouring composition preferably comprises up to 25 wt % of one or more sulphur-containing nucleophiles, preferably up to 15 wt %, more preferably up to 10 wt %, for example up to 7 wt %.

The above amounts refer to the total amount of all sulfur-containing nucleophiles in the colouring composition (for application as a single composition).

The colouring composition may comprise a mixture of one or more thiols and/or one or more sulfite-containing species. Preferably the colouring composition comprises at least one thiol and at least one sulfite containing species.

The weight ratio of thiol to sulfite containing species in the colouring composition is preferably from 1:5 to 5:1, more preferably from 1:3 to 3:1, suitably from 1:1.5 to 1.5:1.

Preferably the colouring composition comprises at least 0.1 wt % of one or more thiols, preferably at least 0.5 wt %, more preferably at least 1 wt %, for example at least 1.5 wt %. The colouring composition preferably comprises up to 15 wt % of one or more thiols, preferably up to 10 wt %, more preferably up to 6 wt %, for example up to 4 wt %.

Preferably the colouring composition comprises at least 0.1 wt % of one or more sulfite containing species, preferably at least 0.5 wt %, more preferably at least 1 wt %, for example at least 1.5 wt %. The colouring composition preferably comprises up to 15 wt % of one or more sulfite containing species, preferably up to 10 wt %, more preferably up to 6 wt %, for example up to 4 wt %.

The dye compound used in the present invention may be selected from any known class of a dye other than the class of reactive dyes. Preferably it is a cosmetically approved dye. Suitably the dye may be selected from the classes of direct dyes, basic dyes, acid levelling dyes, premetallised dyes (including 2:1 premetallised acid dyes and 1:1 premetallised acid dyes), acid milling dyes, food dyes, natural dyes, leather dyes, pigment dyes, sulphur dyes, solvent dyes, vat dyes, ingrain dyes, mordant dyes, fluorescent brightening agents and disperse dyes.

Preferably the dye is selected from the classes of direct dyes, acid levelling dyes, premetallised dyes (including 2:1 premetallised acid dyes and 1:1 premetallised acid dyes) and acid milling dyes. Also useful are water-solubilised vat dyes, for example those based on sulfate esters of hydroquinone-based dyes.

The skilled person would be familiar with the above-mentioned classes of dye and would understand the types of compounds which fall within each class.

The Colour Index International is a standard classification system for dyes and pigments which contains historic, proprietary, generic names and generic numbers that have been applied to colours. It was first published in 1924 and has been updated and reprinted since. The $2^{nd}$ (1956), $3^{rd}$ (1971) and $4^{th}$ (2002) editions are jointly published and maintained by the Society of Dyers and Colourists (SDC) (UK) and American Association of Textile Chemists and Colourists (AATCC).

There are four volumes of the Colour Index International which classify the colorants by constitution and by application.

Volumes 1 to 3 classify the colorants according to application type resulting in 19 different classes with each colorant being given a CI generic name (e.g. CI Acid Orange 7 etc). The information provided for each colorant includes chemical type (azo, anthraquinone etc), CI constitution number, dyeing and printing behaviour and fastness properties.

Volume 4 of the Colour Index classifies colorants according to their constitution (i.e. their chromophoric system). When these colorants are divided by their chromophoric system, then 27 classes are established. Some of the preferred 19 classes of colorants and 27 chromophoric classes from which dyes useful in the present invention may be selected are further described herein.

Dye classes are often defined in terms of the way in which they colour the fibres on which they have been traditionally used, for example wool or cotton. However compounds in all of the classes could effectively be used in the present invention to dye keratinous material, for example hair.

Acid dyes are typically water soluble anionic dyes that contain one or more sulphonic acid groups, usually as the sodium salt, carboxylic acid groups or hydroxyl groups (less common). The structure on which the dyes are based depends on the colour. Acid dyes can be based on a number of chromophores, which tend to dictate the colour of the dye. For example, blue acid dyes are often based on an anthraquinone moiety, although some may be azo based, formazan or phthalocyanine based. Red, orange and yellow acid dyes tend to be based upon azo moieties, for example CI Acid Red 138:

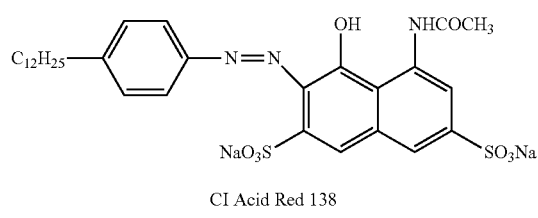

CI Acid Red 138

Acid dyes are traditionally used for dyeing wool and polyamide fibres under acidic to neutral conditions. There are three main types of acid dyes:

i) Acid levelling dyes, which have the highest level dyeing properties. They can be used in combination with other levelling dyes in order to give trichromatic shades. They are relatively small molecules which exhibit high migration before fixation.

ii) Acid milling dyes, which tend to have more side chains and sulfonyl groups, and are larger in size than levelling dyes. Acid milling dyes in general are not combinable to form trichromatic shades, and tend to be used on their own.

iii) Metal complex acid dyes, which combine transition metals such as copper, zinc and chromium with dye precursors to produce a metal complex acid dye.

Direct dyes are a very large dye class that are traditionally used mainly for the dyeing and printing of cellulosic fibres. The coplanar, linear high molecular weight dyes solubilised by sulphonate groups dye cotton directly without recourse to a mordant—hence the name direct dye. Examples include CI Direct Red 8 and CI Direct Black 19:

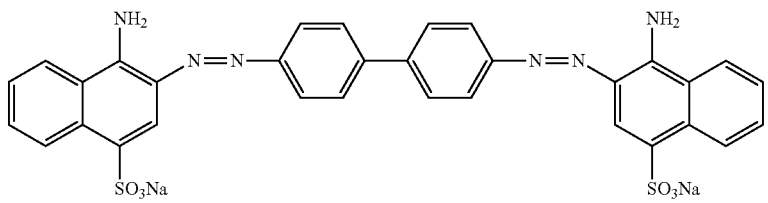

CI Direct Red 8 (Congo Red)

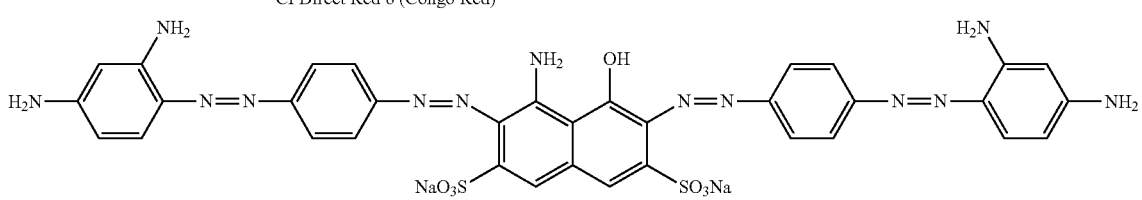

CI Direct Black 19

Basic (cationic) Dyes are water soluble cationic dyes that characteristically are of high tinctorial strength and brilliance, for example CI Basic Red 26:

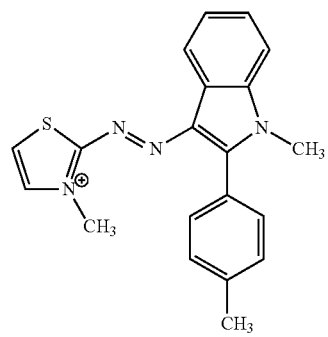

CI Basic Red 26

Disperse Dyes are sparingly soluble in water and are usually employed as dispersions. However dyeing takes place from a saturated aqueous solution. The dyes are traditionally used for the dyeing/printing of hydrophobic fibres. An example is CI Disperse Blue 73:

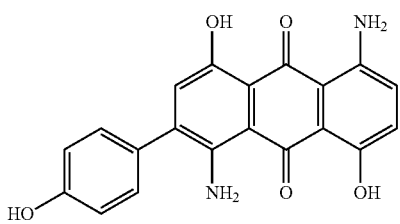

CI Disperse Blue 73

Solvent Dyes are water insoluble dyes, for example CI Solvent Blue 11:

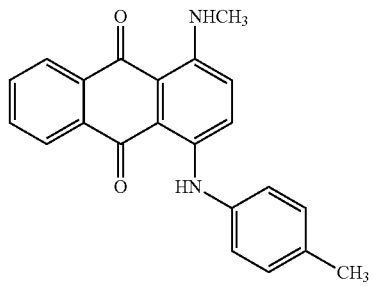

CI Solvent Blue 11

Food dyes include both acid and basic dyes.

Ingrain Dyes are usually based on phthalocyanine moieties and form water insoluble complexes inside the fibre.

Leather Dyes are dyes selected from other classes (e.g. acid, direct) because of their ability to dye leather, for example CI Acid Red 34:

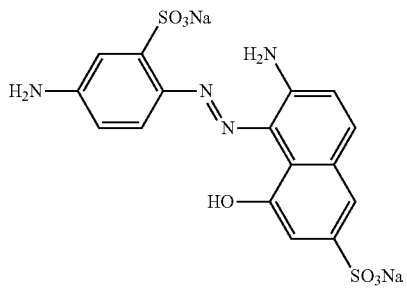

CI Acid Red 34

Methods of dyeing with mordant dyes involve pre-treating a textile with a solution of a metal salt. Mordant dyes are thus typically water soluble anionic dyes that contain OH, $NH_2$ and COON groups which are capable of forming a stable coordination complex with a metal ion on the inside of the fibre. An example is CI Mordant Black 9. This dye is a complex in which 2 ligands having the structure below are coordinated to a $Cr^{3+}$ ion:

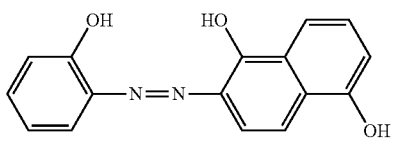

Natural Dyes are obtained from animal or vegetable matter with little, if any, chemical processing. Examples include Kermes and CI Natural Red 4:

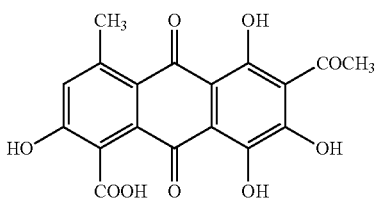

Kermes

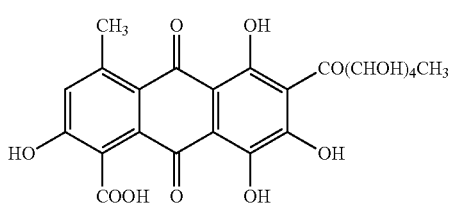

CI Natural Red 4 (Cochineal)

Vat Dyes are water insoluble dyes that contain at least two conjugated carbonyl groups that allow the dye to be converted, by alkaline reduction, to the water soluble leuco derivative which is then applied to the substrate. Subsequent oxidation of the leuco compound within the fibre regenerates the insoluble parent vat dye in situ within the fibre. Indigo is an example of such a dye:

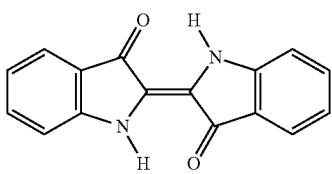

CI Vat Blue 1 (Indigo)

Particularly useful vat dyes include those based on indigo which have been sulphated for example by reduction and then treatment with chlorosulfonic acid. One such compound is Indigosol O:

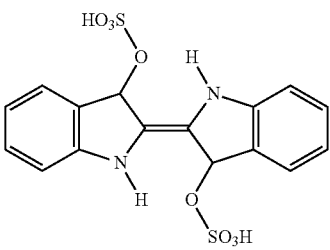

Other useful vat dyes include those having an anthroquinone structure, for example Indanthren Blue RS:

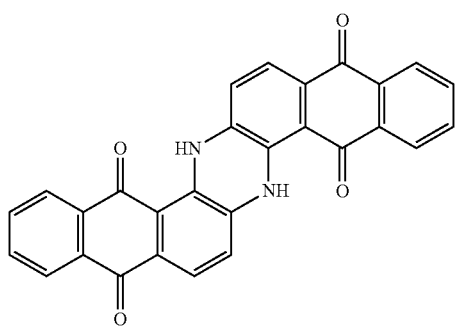

This compound could also be rendered water-soluble by reduction and sulfonation. Polyanthraquinone-based vat dyes having a wide range of colours are known.

Sulphur Dyes are chemically complex, and the structure of the dye is often unknown. Generally they are prepared by heating aromatic compounds with sulphur to produce disulphide (S—S) linkages between the aromatic components.

Fluorescent brightening agents have the ability to absorb incident light in the UV region and to re-emit some of this absorbed light at higher wavelengths, normally in the blue region of the visible spectrum. An example is CI Fluorescent Brightener 46:

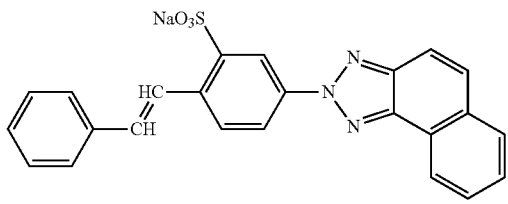

CI Fluorescent Brightener 46

The skilled person would be aware of the above dye classed and would readily appreciate which types of dyes fall within the stated classes.

Examples of suitable direct dyes for use in the present invention include those sold under the trademarks Solar Orange 2GL, Solar Yellow BG, Pyrazol Scarlet SE, Pyrazol Violet 3R, (available from Clariant GmbH (Germany)), Benzo Brilliant Blue 6BS, Levacell Blue S (available from Bayer AG, Germany).

Examples of suitable basic dyes for use in the present invention include those sold under the trademarks Maxilon Red SL (available from Huntsman Textile Effects), Basazol Orange 03P (BASF), Astrazon Blue BG (available from DyStar (UK) Ltd).

Examples of suitable acid levelling dyes for use in the present invention include those sold under the trademarks Polar Red BL (available from Huntsman Textile Effects), Supranol Blue GWL (available from Bayer AG).

Examples of suitable premetallised dyes for use in the present invention include those sold under the trademarks Neolan Red P (available from Huntsman Textile Effects), Lanasyn Red SG (available from Clariant GmbH (Germany)), Neutrilan Orange K-RL (available from Crompton & Knowles), Gryfalan Violet RL (available from Ciech SA), Acidol Red 2BE-N (available from BASF).

Examples of suitable acid milling dyes for use in the present invention include those sold under the trademarks Lanaset Blue 2R, Erionyl Blue RL, Tectilon Blue 6G (available from Huntsman Textile Effects), Telon Blue AR01 (available from DyStar), Nylosan Violet F-BL 180 (available from Clariant GmbH (Germany)).

Preferred dyes for use in the compositions of the present invention are from the Telon Range (available from Dystar) and include Black AMF, Blue AR01, Yellow A2R, Red A2R, Yellow M-5GL, and Navy AMF.

Although the above mentioned trade names may change, the skilled person would be able to consult the Colour Index International to identify the dye compound and find a current manufacturer.

As mentioned above, dyes may also be defined in terms of their chemical structure, that is by reference to the chromophore moiety that they include.

Suitable dye compounds for use in the present invention may include a chromophore moiety based on one or more chromophores selected from the group of nitroso, nitro, azo, stilbene, carotenoid, diphenylmethane, metal complex azo, triphendioxazine, triarylmethane, xanthene, acridine, quinoline, methine, thizaole, indamine, indophenol, azine, oxazine, thiazine, lactone, aminoketone, hydroxyketone, formazan complexes, anthraquinone, indigoid, phthalocyanine and natural colourants.

Preferably the chromophore is selected from azo, metal complex azo, triphendioxazine, anthraquinone, phthalocyanine and formazan complexes.

Most preferably the dye compound includes a chromophore selected from azo, anthraquinone, phthalocyanine and formazan complexes.

Examples of dye compounds including some of the above chromophore moieties include the following:

Azo
Monoazo
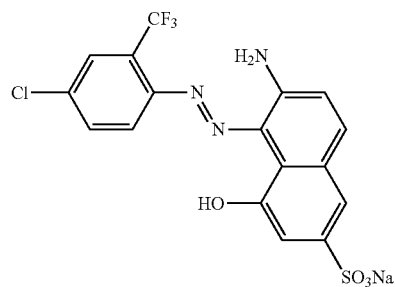
CI Acid Red 266
Disazo
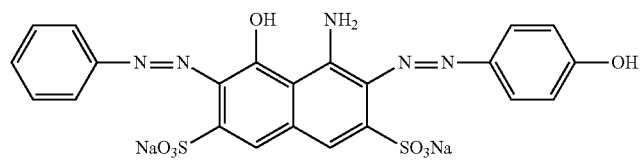
CI Acid Black 1
Trisazo
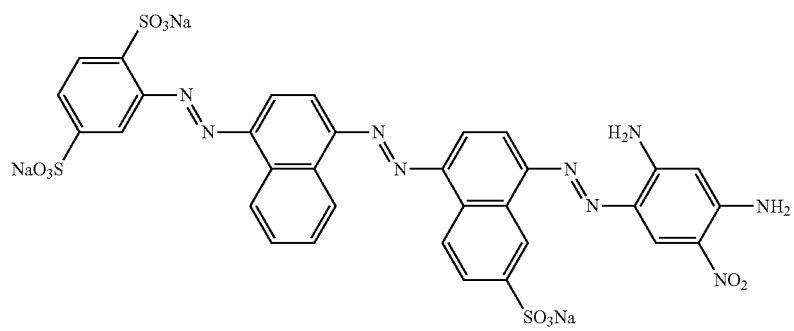
CI Direct Red 103
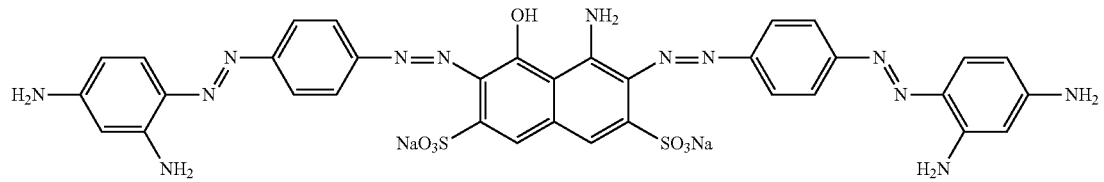
CI Direct Black 19
Polyazo
Stilbene
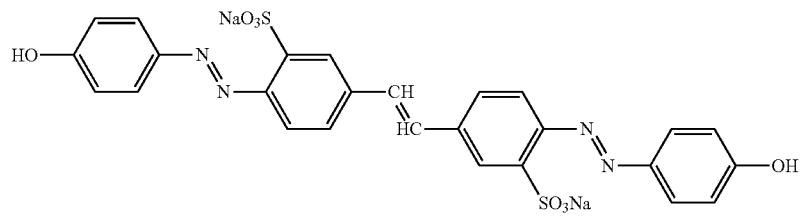
CI Direct Yellow 19
Carotenoid -continued
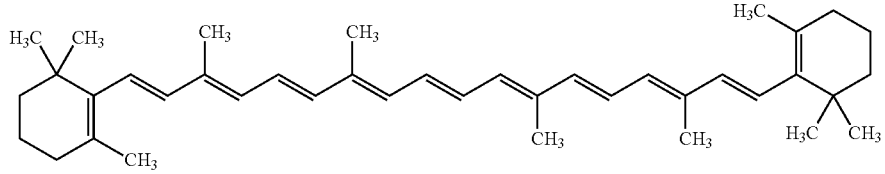
CI Food Orange 5
Quinoline
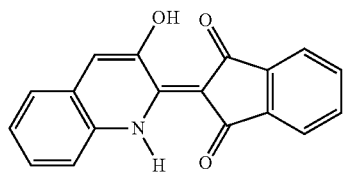
CI Disperse Yellow 54
Methine
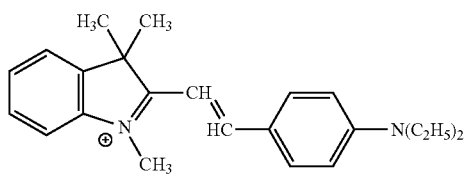
CI Basic Violet 16
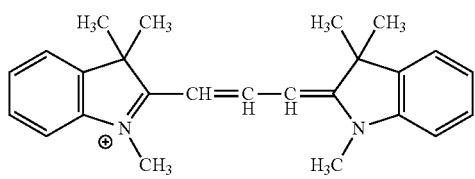
CI Basic Red 12
Thiazole
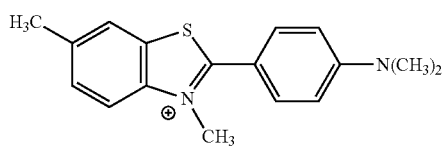
CI Basic Yellow 1
Indamine
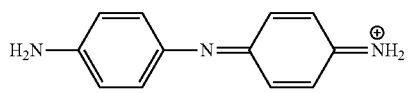
Phenylene Blue
Indophenol
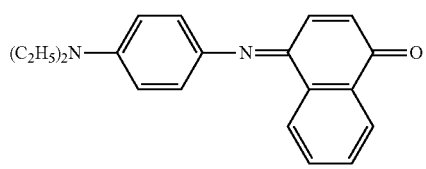
CI Solvent Blue 22
Azine

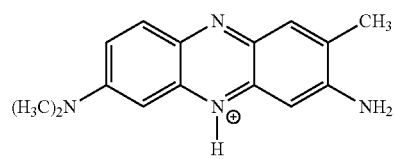
CI Basic Red 5
Oxazine
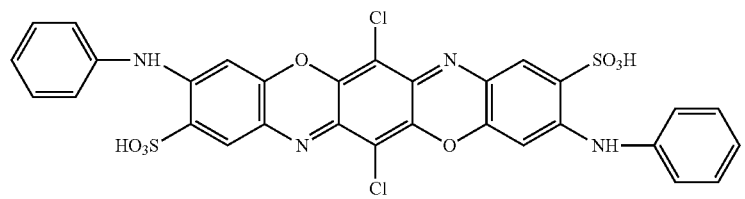
CI Direct Blue 106
Thiazine
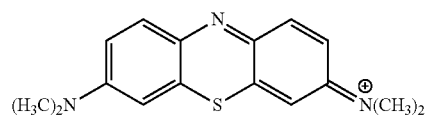
CI Basic Blue 9
Metal complex azo
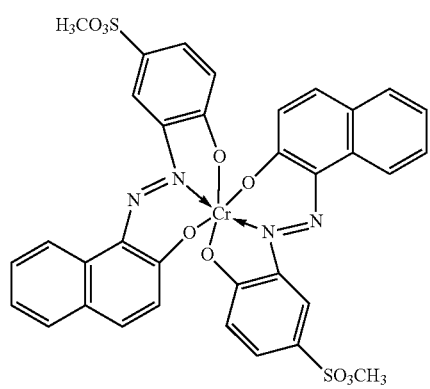
C.I. Acid Violet 78
Formazan
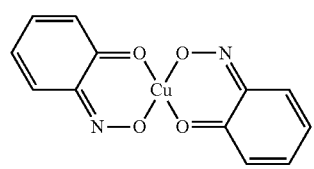
CI Acid Green 1
Napthol Green B
Triphendioxazine

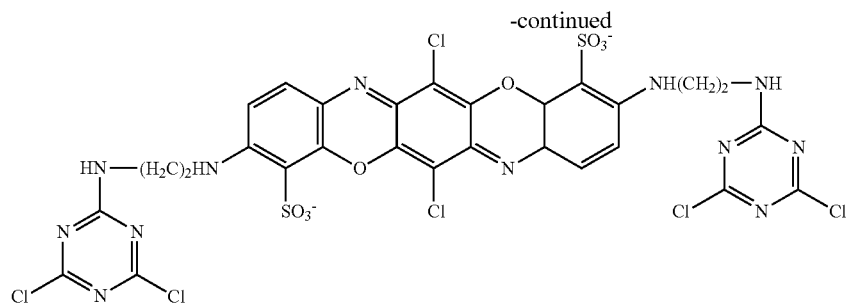

CI Reactive Blue 163

The compositions of the present invention may include a mixture of two or more dye compounds selected from classes other than the class of reactive dyes. These may be selected from the same and/or different classes. They may be combined in a specific ratio to achieve a desired colour or other visual effect.

The colouring composition preferably comprises at least 0.001 wt % of the dye compound, preferably at least 0.1 wt %, more preferably at least 1 wt %, for example at least 2 wt %. The colouring composition suitably comprises up to 30 wt % of the dye compound, preferably up to 25 wt %, more preferably up to 20 wt %, for example up to 15 wt %.

The above amounts refer to the total amount of all dye compounds of classes other than reactive dyes present in the colouring composition (for application as a single composition). Commonly mixtures of two or more dyes will be included, the relative amount being dependent on the desired shade required and the preparation of such mixtures will be readily understood by those skilled in the art.

In some embodiments, the colouring composition may further comprise one or more reactive dyes in addition to the one or more dyes of other classes present in the composition.

The colouring compositions of the present invention optionally contain urea. Without being bound by theory it is believed that urea helps to solubilise the dye compounds in the composition and/or denatures keratinous proteins found in hair (and animal fibres) and increases the rate of reaction with the fibre substrate.

Urea may suitably be present in the composition in an amount of at least 2 wt %, and preferably at least 5% wt.

Urea may suitably be present in an amount up to 40% wt of the composition, preferably up to 30% wt, most preferably up to 20% wt.

The colouring composition preferably comprises one or more solvents or diluents.

Suitable diluent materials for use in colouring compositions described herein may be selected from those specified on the INCI list(International Nomenclature of Cosmetic Ingredients list). This is drawn up by the Scientific Committee on Consumer Products (SCCP) managed by the Directorate-General for Health and Consumer Protection of the European Commission. The SCCP approve a list of chemicals for use in cosmetics which is referred to as the INCI list.

Water is the preferred diluent for use in the present colouring compositions. However, such compositions may include one or more further solvents as additional diluent materials. Generally, solvents suitable for use in the colouring compositions of the present invention are selected to be miscible with water and innocuous to the skin. Solvents suitable for use as additional diluents herein include C1-C20 mono- or polyhydric alcohols and their ethers, glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, propylene glycol, ethylene glycol monoethyl ether, and mixtures thereof. Water is the preferred principal diluent in the compositions according to the present invention. Principal diluent, as defined herein, means, that the level of water present is higher than the total level of any other diluents.

Preferred dye compounds for use in the present invention are water soluble and completely dissolve to provide a substantially homogeneous aqueous colouring composition. However embodiments including dye compounds that are not completely water soluble or are water insoluble are also within the scope of the invention. In such embodiments the dye compound may suitably be present in the composition in the form of a suspension. Alternatively the dye compound may be first dissolved in a cosolvent. This may for example be a water miscible cosolvent.

The diluent may suitably be present in an amount of at least 20 wt %, preferably at least 40 wt %, more preferably at least 60 wt %. It may be present in an amount of up to 98 wt %, preferably up to 90 wt %, for example up to 80 wt %. The above amounts refer to all diluents present in the composition (including for example any cosolvent).

The colouring compositions of the present invention may further comprise one or more surfactants. Suitable surfactants for use in compositions of the present invention may be found on the INCI list. Suitable surfactants for inclusion in the compositions of the invention generally have a lipophilic chain length of from about 8 to about 22 carbon atoms and can be selected from anionic, cationic, nonionic, amphoteric, zwitterionic surfactants and mixtures thereof.

Suitable surfactant compounds for use in the present invention are of the conventional type known for use in hair dye formulations and will be well understood by those skilled in the art. Preferred surfactants are those favoured by the cosmetic industry. These are typically gentle and non-allergenic and include, for example cocamidopropyl betaine and laurylamidopropyl betaine.

The colouring composition may typically comprise from 0.1 to 10 wt % of one or more surfactants, preferably from 0.5 to 2.5 wt %.

In addition to the surfactant compounds detailed above, additional amounts of compounds of this type may be present as a conditioning agent.

The hair colouring compositions of the present invention may additionally include a thickener, suitably a cosmetically approved thickener. This is preferably present in an amount of from 1 to 20 wt %, preferably from 2 to 10 wt %. Thickening agents suitable for use in the compositions herein include those specified on the INCI list. Preferred thickening agents suitable for use in the compositions of the present invention include oleic acid, cetyl alcohol, oleyl alcohol, sodium chloride, cetearyl alcohol, stearyl alcohol, synthetic thickeners such as Carbopol and Glucamate™ (The Lubrizol Corp, USA), Aculyn polymers (Rohm and Haas, USA) and mixtures thereof. An especially preferred thickener for use herein is hydroxyethyl cellulose.

The colouring compositions of the present invention preferably have a pH in the range of from 5 to 13, preferably from 8 to 11.5, more preferably from 9 to 10.5. In order to maintain such a pH the compositions may contain one or more optional pH control agents.

Preferred pH control agents for use herein include those specified on the INCI list, for example 2-amino-2-methyl-1-propanol, ammonium hydroxide, and sodium hydroxide.

The colouring compositions of the present invention may be provided in any suitable form. For example they may be provided as a solution, paste, cream, lotion, gel, mousse foam, spray or the like. The composition is suitably of a viscosity which enables it to spread across the head easily during the hair dyeing process, and then stay in position on the head when required.

In preferred embodiments of the method of the first aspect of the present invention in which a single composition of the second is applied to the material (suitably hair), the composition is preferably applied and maintained in contact with the material at a temperature of at least 0° C., preferably at least 10° C., for example at least 20° C. It may suitably be applied and maintained at a temperature of up to 70° C., for example up to 60° C. or up to 50° C. A temperature of approximately 40° C. is particularly preferred. As will be appreciated by the person skilled in the art, when the material being dyed is human hair a suitable hood may be used to achieve the desired temperature.

The composition is preferably contacted with the material for a period of at least 1 minute, preferably at least two minutes, more preferably at least 5 minutes, for example at least 10 minutes.

It may be contacted with the material for a period of up to 1 hour, suitably up to 45 minutes, preferably up to 30 minutes, for example up to 20 minutes.

In an alternative embodiment the method of the first aspect of the present invention may comprise carrying out steps (a) and (b) sequentially. In such embodiments, the method preferably comprises applying to the material a first composition comprising a sulphur-containing nucleophile and then applying to the material a second composition comprising a dye compound, although the compositions could also be applied in the opposite order.

The amounts of sulphur-containing nucleophile and dye compound present in each of these compositions and the treatment times and temperatures are selected to provide an equivalent hair colouring effect to that achieved when using the single colouring compositions described herein, such as are defined in relation to the second aspect. It is within the expertise of the skilled person to be able to readily select the appropriate amounts and treatment conditions for this two step method.

The colouring composition of the second aspect or the first and second compositions used in the two-step method of the first aspect may be applied to the hair by any suitable means. Such methods are well known to those skilled in the art and include for example brushing the composition (which may suitably be in the form of a paste) onto the hair.

The compositions may be suitably applied to hair at a liquor ratio of from 10:1 to 0.5:1, preferably from 5:1 to 1:1, for example from 3:1 to 2:1.

The compositions may suitably be rinsed from the hair with warm water.

Optionally, an after-treatment may be applied to the hair.

In some embodiments an after-treatment solution is applied to the hair comprising aqueous hydrogen peroxide. A composition comprising from 20 to 60 wt %, for example 30 to 40 wt % hydrogen peroxide may suitably be applied, preferably using the same liquor ratio as described above and allowed to remain on the hair for a period of 1 to 20, preferably 5 to 10 minutes.

In some embodiments, in an after-treatment, the hair may be treated with a composition which can impart a particular property, for example improved wash fastness or soft handle. The composition may be provided in any suitable form for example a solution, cream, foam, mousse, spray or gel. One suitable after-treatment comprises applying a composition comprising a hair conditioning agent. Such conditioning compositions are well known to those skilled in the art and any commercially available conditioning composition could be used. Non-limiting examples of suitable commercially available "off-the-shelf" conditioning agents include Pantene Pro-V® Intensive Hair repair treatment, L'Oreal Elvive Re-Nutrition® or John Freida Frizz-Ease Critical Care Miraculous Recovery.

In preferred embodiments of the present invention in which a single composition is applied to the material, this composition may be first prepared from two precursor compositions.

Thus a third aspect of the present invention comprises a method of preparing a colouring composition of the second aspect, the method comprising the admixture of a first precursor composition comprising a dye compound selected from a dye class other than the class of reactive dyes and a second precursor composition comprising a sulphur-containing nucleophile.

The amount of each component present in each of the first and second precursor compositions is suitably selected such that admixture of the two precursor compositions in an appropriate ratio provides the compositions of the second aspect. Examples of suitable precursor compositions are given in the examples described herein. However these are intended to be in no way limiting and alternative precursor compositions which may be mixed to provide compositions of the second aspect for use in the method of the first aspect are also within the scope of the present invention. The person skilled in the art would readily understand how to prepare such compositions. Either or each of the first and second precursor compositions may comprise one or more of the additional ingredients as mentioned herein. When urea is present, this is preferably provided in the first precursor composition but may alternatively or additionally be included in the second precursor composition.

In a fourth aspect the present invention provides a packaged hair colouring product. This may comprise a composition of the second aspect along with suitable packaging. Preferably however it comprises a first package comprising a first precursor composition comprising a dye compound selected from a dye class other than the class of reactive dyes and a second package comprising a second precursor composition comprising a sulphur-containing nucleophile.

The first package and second package may be of any suitable form.

In one embodiment the packaged hair colouring product may be provided in a bicompartment container in which the first precursor composition is held in a first compartment and the second precursor composition is held in a second compartment, of the same container. Preferably the bicompartment container is arranged to deliver the first and second precursor compositions to the same locus. This may be achieved by providing adjacent outlets from the first and second compartments. Alternatively, the first and second compartments may deliver the first and second precursor compositions into a common passageway in which they are contacted prior to exiting the container through a single outlet. Bicompartment containers of this type are known to the person skilled in the art. One such example is a squeezable tube (known as a "dual tube") having two compartments comprising the two precursor compositions. Squeezing the tube causes the two compositions to be delivered through adjacent outlets such that they come into immediate contact with each other on exiting the container. Other embodiments of bicompartment containers also include bottles or canisters for holding mousses, gels or sprays which are provided with a single actuator which effects delivery of the two precursor compositions to the same locus via the same or adjacent outlets.

Alternatively the hair colouring product of the present invention may be provided as two discrete precursor compositions which are packaged separately in individual containers. In such embodiments, the packaged hair colouring product may further comprise instructions for preparing the active colouring composition of the second aspect.

In some embodiments the packaged hair colouring product may further comprise a utensil for application of the colouring composition to the hair, for example a brush or a spatula. In some embodiments the packaged product may further comprise equipment for preparing the colouring composition from the precursor compositions, for example a mixing container and/or stirrer.

In some embodiments in which the packaged hair product comprises separate first and second packages comprising first and second precursor compositions which are combined prior to application to the hair, each of the precursor compositions may be provided in any suitable form. Each may be a solid, a liquid, a paste or gel.

In some embodiments each of the first and second precursor compositions may be a solid to which a solvent, suitably water must be added to form the colouring composition of the second aspect.

In some embodiments one of the first or second precursor compositions is a liquid composition and the other is a solid composition. Admixture of the first and second precursor compositions may in such embodiments directly form a composition of the second aspect.

Where one or both of the first and second compositions is a paste, gel or cream a composition of the second aspect may be directly obtained on admixture.

In some embodiments the first and second precursor compositions may each contain part of a bi-component thickener such that mixing the compositions leads to an increase in viscosity. In such a manner two liquid compositions for example could be combined to form a paste or cream having a consistency to enable it to be easily applied to the hair without running off. Suitable bi-component thickeners are known to the person skilled in the art. It would also be possible to include thickeners which changes viscosity upon a change in pH.

The packaged hair colouring product of the present invention preferably comprises instructions for colouring hair.

In some embodiments in which the product comprises first and second packages comprising first and second precursor compositions, the packaged hair colouring product may further comprise instructions for preparing the active hair colouring composition.

It has been surprisingly found that hair coloured by the method of the present invention has superior wash fastness compared to hair coloured by methods of the prior art. For example, a so-called "permanent" colouring composition of the prior art of the type formed in situ from dye precursor compounds would show some colour fading following five shampooing applications. However hair coloured by the method of the present invention suitably shows substantially no fading after ten washes, preferably after fifteen washes, more preferably after twenty washes. Thus the method of the first aspect of the present invention may be regarded as a method of permanently dyeing hair.

Without wishing to be bound by theory it is believed that the dye compounds used in the present invention may form a variety of types of interactions with the hair fibres for example electrostatic interactions, hydrophobic interactions and aromatic $\pi$-$\pi$ interactions. The interactions may be dye-dye interactions or dye-keratin interactions.

Without wishing to be bound by any theory it is believed that the sulfur-containing nucleophile applied to the hair in the method of the present invention may react with some disulfide bonds in the keratin fibres cleaving them and allowing them to swell. This may facilitate dye diffusion leading to increased interactions and thus lead to improved wash fastness.

The method of the present invention has been found to be particularly effective when used to colour hair that has first been bleached. Again without wishing to be bound by theory it is believed that pre-bleaching may help open up the structure of the hair and thus allow better penetration of the dye within the hair.

Thus the method of the present invention may include a first step of bleaching the hair prior to colouring to provide a lighter initial colour and a different overall result.

This first bleaching step may be carried out by use of percarbamic acid and/or a diacyl percarbamate, generated in situ by the method of the applicant's earlier patent EP 1313830B.

Preferably however the bleaching is carried out using the improved mild bleaching method described in the applicant's co-pending applications GB0816943.5, GB0907800.7 and PCT/GB2009/051157.

This mild bleaching method preferably comprises applying to the hair a composition comprising at least 10 wt % of ammonium carbonate, ammonium carbamate or a mixture thereof and a source of hydrogen peroxide. Preferred features of the bleaching step are as defined in the above-mentioned applications.

If it is desired to remove colour from the hair following the colouring method of the present invention, this could be achieved by applying to the hair a composition comprising a chemical agent able to reduce the chromophore moiety. Such compositions are well known to those skilled in the art and the removal of the colour in such circumstances is readily achieved.

However in preferred embodiments colour removal is effected using a colour removal method such as is described in the applicant's co-pending applications GB0816943.5 and PCT/GB2009/050233.

As described in these applications the present inventors have developed a particularly effective composition and method which can be used to remove colour from dyed hair. As has been described in the above-mentioned applications, the colour removal system may be used to remove colour from hair dyed using reactive dyes. The inventors have further found that this colour removal method is particularly effective at removing colour from hair treated according to the method of the present invention. Thus, the present invention may further include a hair colour removal method.

The colour removal method is not a bleaching method. Indeed the colour removal method of the present invention is particularly advantageous because it does not involve oxidative bleaching of the hair and thus avoids the damage that colour removal by bleaching may cause.

The hair colour removal method of the present invention preferably comprises applying to dyed hair, preferably hair dyed by the method of the first aspect, a colour removal composition comprising a nucleophile, or a precursor thereof. Preferably the colour removal composition comprises a sulfur-containing nucleophile, or a precursor thereof. Suitable sulfur-containing nucleophiles include thiocyanate, thioglycolic acid, thiocarbamate, carbamoylsulphinic acid and mixtures and/or salts thereof. Alternatively and/or additionally, the colour removal composition may comprise a nucleophile precursor. One suitable nucleophile precursor is thiourea dioxide. Thiourea dioxide is not nucleophilic in itself but rearranges to form formamidine sulfinic acid which hydrolyses to form the nucleophilic species $HSO_2^-$ (hydrosulfoxylate).

In especially preferred embodiments the sulfur-containing nucleophile comprises a salt of sulphoxylic acid of formula $HSO_2^-$ $^+M$. M is preferably hydrogen, an alkali metal or a quaternary ammonium species. Such salts may suitably be generated from formamidine sulphinic acid, dithionite ($S_2O_4^{2-}$) or the compounds sold by BASF under the trade marks Formosul ($HOCH_2SO_2^-Na^+$) and Decralin (($HOCH_2SO_2^-)_2Zn^{2+}$).

Under acidic conditions formamidine sulphinic acid exists as the thiourea dioxide tautomer but under mildly alkaline conditions the formamidine tautomer is formed which hydrolyses to release $HSO_2^-$ $^+M$ which is believed to be the active dye removal agent. It is also possible to use mixed formamidine/carbamoyl sulphinic acids to generate the reactive species.

The colour composition comprises preferably at least 0.1 wt % of the sulfur-containing nucleophile or precursor thereof, for example thiourea dioxide, more preferably at least 1 wt %, most preferably at least 4 wt %.

Suitably the colour removal composition comprises up to 60 wt % of the sulfur-containing nucleophile or precursor thereof, for example thiourea dioxide, preferably up to 45 wt %, more preferably up to 30 wt % and most preferably up to 15 wt %.

In some preferred embodiments where the hair has been dyed using a premetallised dye comprising a transition metal (for example cobalt or chromium), the colour removal composition further comprises a sequestrant. Any suitable sequestrant known to those skilled in the art may be used. Preferred sequestrants include N-methyl taurine, phosphonates and amine alkyl phosphonates, for example those sold under the trade mark BriQuest and DeQuest, ethylenediaminetetraacetic acid (EDTA) and ethylenediamine disuccinic acid (EDDS).

The sequestrant, when present, is preferably present in an amount of from 1 to 20 wt %, more preferably 5 to 10 wt %.

The colour removal composition may further comprise one or more of a swelling agent, an activator, a diluent, a conditioning agent, a pH buffer and a thickener.

Other optional excipients may also be present. Preferred ingredients for use as a conditioning agent and the like include those detailed on the INCI list.

Suitable swelling agents include urea.

The colour removal composition preferably comprises at least 0.1 wt % urea, preferably at least 1 wt %, more preferably at least 3 wt %, most preferably at least 5 wt %.

Suitably the colour removal composition comprises up to 60 wt % urea, preferably up to 45 wt %, more preferably up to 30 wt % and most preferably up to 15 wt %.

Suitable activators include divalent and trivalent metal species, for example divalent and/or trivalent ions of zinc, magnesium, aluminium and calcium. Preferably the activator includes zinc or especially magnesium ions. The divalent or trivalent ions may be provided in any suitable form. Preferably they are provided as salts, for example carbonates, sulfates, chlorides, acetates or formates. More preferably they are provided as organic acid salts, for example formate or acetate. Suitably the activator may be selected from zinc acetate, magnesium acetate, zinc oxide, magnesium carbonate, zinc sulphate, aluminium acetate, calcium acetate and mixtures thereof. Zinc acetate and magnesium acetate are particularly preferred.

Acetate or formate salts of divalent or trivalent metals when present may be used directly in the colour removal compositions of the present invention. Alternatively the corresponding acid and a different metal salt may be used, for example magnesium sulphate and acetic acid.

The colour removal composition comprises preferably at least 0.1 wt % of one or more activators, more preferably at least 1 wt %, most preferably at least 4 wt %.

Suitably the colour removal composition comprises up to 60 wt % of one or more activators, preferably up to 45 wt %, more preferably up to 30 wt % and most preferably up to 15 wt %.

The preferred diluent is water. This suitably present in an amount of from 10 to 90 wt %.

Suitable pH buffers include 2-amino-2-methyl-1-propanol.

Suitably the colour removal composition has a pH of from 6 to 12, more preferably from 7.5 to 10.5, and most preferably from 8.5 to 9.5.

A preferred thickener is hydroxyethylcellulose. Preferably the colour removal composition comprises from 1 to 20 wt % of thickeners.

In order to maximise the shelf life of the colour removal composition, it can be packaged as a two component system which could be mixed together shortly before use. By utilising a two pack system, it is possible to make two liquid solutions, that when combined produce a thickened product which is more suitable for use on hair. This can be achieved for example by using a cosmetically approved thickener whose viscosity changes with pH. Suitable ingredients for the colour removal formulations can be found in the INCI list or will be well known to those skilled in the art. Such systems are described above in relation to the packaged hair colouring compositions of the fifth aspect of the present invention.

In the colour removal method of the present invention, the colour removal composition is suitably applied to the hair and maintained on the head at a temperature of from 10 to 75° C., preferably from 20 to 70° C., more preferably from 30 to 65° C.

When removing colour from human hair at temperatures above ambient temperature a suitable hood can be employed to achieve the required temperature.

Suitably complete colour removal is effected after a period of 5 to 60, for example 15 to 30 minutes.

Suitably the colour removal composition is left in the hair for a period of from 0.1 to 60 minutes, preferably 0.5 to 30 minutes for example 1 to 15 minutes.

The colour removal method of the present invention has been found to be very effective. Hair has been found to return to its original colour prior to being dyed without any visible damage occurring. In embodiments in which an initial bleaching step has been carried out, hair has been found to return to its bleached colour.

This method offers considerable advantages over colour removal methods of the prior art which rely on bleaching the hair. Such bleaching colour removal methods of the prior art cause considerable damage to hair (particularly in the case of hair which is repeatedly dyed and oxidatively bleached) and often do not provide the original colour.

It is also known from the prior art to use aminomethanesulfinic acid for colour removal. Under the conditions used, this would not act as a nucleophile but for the avoidance of doubt, the nucleophilic colour removal species of the present invention does not comprise aminomethanesulfinic acid. In any case aminomethanesulfinic acid may, like oxidative bleaching agents, cause damage to the hair and is not as effective as the colour removal systems of the present invention for removing colour applied by the method of the invention.

The present invention thus provides a hair treatment method comprising the steps of:
(a) optionally bleaching hair by applying a bleaching composition comprising from ammonium carbonate or a divalent metal cyanate and a source of hydrogen peroxide;
(b) dyeing the hair by the method of the first aspect; and
(c) optionally removing colour from the hair by applying a colour removal composition comprising nucleophilic colour removal species.

Preferred aspects of each of steps (a), (b) and (c) are described above. Steps (b) and (c) may be repeated without any significant damage occurring to hair. Preferably steps (b) and (c) may be each repeated two or more, preferably five or more, for example ten or more times without any significant increased damage to the hair being observed.

Step (a) is an optional mild initial bleaching step. This is carried out if it is desired to lighten the initial colour of hair prior to a first dyeing step. However, once a first colour has been applied, there is no need to again bleach the hair further to remove this colour as this can be carried out in step (c). Step (a) would be repeated only if a lighter base shade is required. Of course it will also be necessary to bleach new hair which has grown since previous colouring.

Because step (a) and in particular steps (b) and (c) can be carried out rapidly, it would be possible for a user to dye a small portion of hair (either on or off the head) to see exactly the colour that would be achieved and remove this colour if it was not desirable.

The colouring method of the present invention is highly reproducible, rapidly develops to full colour, is resistant to fade and readily removable, and thus offers considerable advantages over the prior art. In particular, when using colouring methods and compositions of the prior art, the final colour of the dyed hair is often unpredictable and relies on the skill of a hairdresser to achieve a close match to the desired colour. The colouring compositions of the present invention can be used in combination with a colour measurement apparatus to accurately measure a desired shade and produce a formula to achieve this colour on the hair. This type of colour match prediction is based on software currently used throughout the textile industry and the paint industry.

The method of the present invention may be used to dye some or all of the hair on the head of a human. Thus all of the hair may be dyed a single colour. Alternatively small sections of the hair may be coloured to provide "streaks" or "highlights/lowlights". In some embodiments new hair at the roots may be coloured to match an existing colour on the body of the hair. A different colour on sections of hair could also be achieved by selective application of the colour removal composition to dyed hair.

According to a further aspect of the present invention there is provided the use of a dye compound selected from a dye class other than the class of reactive dyes in combination with a sulfur containing nucleophile to colour human hair.

Although the present invention relates primarily to the dyeing of a material, for example human hair, in a single application (i.e. only one composition comprising a dye compound or compounds is applied), it could also be used to repeatedly dye and thus gradually build up colour on a material.

For example it may be desired to gradually colour human hair, for example to add colour to grey hair. Thus the method of the first aspect of the present invention may be repeated periodically. This may for example be daily, weekly or monthly. In order to allow a gradual build up of colour to be achieved it would be necessary to adjust the amounts of dye compound present in the compositions applied to the hair accordingly. Such adjustments could be readily made by the person skilled in the art.

In some such embodiments the composition of the second aspect may be provided as a shampooing composition. This may for example be in the form of a "colour enhancing" shampoo which gradually adds colour to the hair upon repeated application.

The invention will now be further described with reference to the following non-limiting examples.

The dyes used in these examples are as follows:

| Example No. | Name | Manufacturer | Dyestuff Class |
| --- | --- | --- | --- |
| 1 | Solar Orange 2GL-P | Clariant | Direct Dye |
| 2 | Maxilon Red SL 200% | CIBA | Basic dye |
| 3 | Polar Red BL | CIBA | Acid Levelling Dye |
| 4 | Supranol Blue GWL | Bayer AG | Acid Levelling dye |
| 5 | Neutrilan Orange K-RL | Crompton & Knowles | 2:1 Premetallised dye |
| 6 | Lanaset Blue 2R | CIBA | Acid milling dye |
| 7 | Erionyl Blue RL 200% | CIBA | Acid milling dye |
| 8 | Tectilon Blue 6G | Huntsman | Acid milling dye |
| 9 | Gryfalan Violet RL | Ciech SA | 2:1 Premetallised Acid Dye |
| 10 | Nylosan Violet F-BL 180 | Clariant | Acid Milling Dye |
| 11 | Acidol Red 2BE-N | BASF | 2:1 Premetallised Acid Dye |

-continued

| Example No. | Name | Manufacturer | Dyestuff Class |
|---|---|---|---|
| 12 | Lanasyl Red SG | Clariant | 2:1 Premetallised Acid Dye |
| 13 | Neolan Red P | Clariant | 2:1 Premetallised Acid Dye |
| 14-17 | Telon Black AMF | DyStar | Acid milling dye |
|  | Telon Blue AR01 | DyStar | Acid milling dye |
|  | Telon Yellow A2R | DyStar | Acid milling dye |
|  | Telon Red A2R | DyStar | Acid milling dye |
|  | Telon Yellow M-5GL | DyStar | Acid milling dye |
| 18 | Telon Navy AMF | DyStar | Acid milling dye |

EXAMPLE 1

A sample of hair having an initial bleached blonde appearance was treated as follows.

| Part 1 | Part 2 |
|---|---|
| 35.46% Urea | 75.76% Water |
| 3.55% Laurylamidopropylbetaine | 2.16% Thioglycolic acid |
| 35.46% Water | 2.16% Sodium sulphite |
| 4.26% Hydroxyethylcellulose | 3.68% 2-amino-2-methyl-1-propanol |
| 21.28% Solar Orange 2GL-P (Clariant) [Direct Dye] | 16.23% Aculyn 28 |

Percentage values in the table above denote the weight of a given component expressed as a percentage of the total weight of the composition of the part in which it is present.

Prepare hair treatment mixture, by mixing 3.2 g of part 1 and 7.9 g of Part 2.

Brush mixture into hair and leave at 40° C. for 15 minutes using a liquor ratio of 2.5:1 (2.5 g of preparation mixture:1 g hair tress).

Rinse with warm water.

Massage an after-treatment solution of 30 g/l hydrogen peroxide soln (36%) using same liquor ratio as above.

Rinse with water

Shampoo

Rinse with water

Dry as required

The resulting hair was an orange colour that was found to exhibit no visible fade or colour change after 20 shampoo washes.

EXAMPLES 2-5

Hair tresses in the following examples were treated using the same procedure as in example 1.

|  |  | Example 2 | Example 3 | Example 4 | Example 5 |
|---|---|---|---|---|---|
| Starting Hair Colour |  | bleached blonde | bleached blonde | bleached blonde | bleached blonde |
| Amount of Part 1 |  | 3.2 g | 3.2 g | 3.2 g | 3.2 g |
| Amount of Part 2 |  | 7.9 g | 7.9 g | 7.9 g | 7.9 g |
| Time |  | 15 mins | 15 mins | 15 mins | 15 mins |
| Temperature |  | 40° C. | 40° C. | 40° C. | 40° C. |
| Final Hair Colour |  | Bright pink | Pale pink | pale blue | dark orange |
| Part 1 | Urea | 35.46% | 35.46% | 35.46% | 35.46% |
|  | Laurylamidopropylbetaine | 3.55% | 3.55% | 3.55% | 3.55% |
|  | Water | 35.46% | 35.46% | 35.46% | 35.46% |
|  | Hydroxyethylcellulose | 4.26% | 4.26% | 4.26% | 4.26% |
|  | Dyestuff | 21.28% Maxilon Red SL 200% | 21.28% Polar Red BL | 21.28% Supranol Blue GWL | 21.28% Neutrilan Orange K-RL |
| Part 2 | Water | 88.16% | 88.16% | 88.16% | 88.16% |
|  | Thioglycolic acid | 2.52% | 2.52% | 2.52% | 2.52% |
|  | Sodium sulphite | 2.52% | 2.52% | 2.52% | 2.52% |
|  | 2-amino-2-methyl-1-propanol | 4.28% | 4.28% | 4.28% | 4.28% |
|  | Hydroxyethyl-cellulose | 2.52% | 2.52% | 2.52% | 2.52% |
| Does the hair exhibit any visible fade or colour change after 20 shampoo washes? |  | No | No | No | No |

EXAMPLES 6-9

Hair tresses in the following examples were treated using the same procedure as in example 1.

|  | Example 6 | Example 7 | Example 8 | Example 9 |
|---|---|---|---|---|
| Starting Hair Colour | Bleached blonde | Bleached blonde | Bleached blonde | Bleached blonde |
| Amount of Part 1 | 3.2 g | 3.2 g | 3.2 g | 3.2 g |

-continued

|  |  | Example 6 | Example 7 | Example 8 | Example 9 |
|---|---|---|---|---|---|
| Amount of Part 2 |  | 7.9 g | 7.9 g | 7.9 g | 7.9 g |
| Time |  | 15 mins | 15 mins | 15 mins | 15 mins |
| Temperature |  | 40° C. | 40° C. | 40° C. | 40° C. |
| Final Hair Colour |  | dark blue | bright blue | bright blue | Dark bluish violet |
| Part 1 | Urea | 35.46% | 35.46% | 35.46% | 35.46% |
|  | Laurylamidopropylbetaine | 3.55% | 3.55% | 3.55% | 3.55% |
|  | Water | 35.46% | 35.46% | 35.46% | 35.46% |
|  | Hydroxyethylcellulose | 4.26% | 4.26% | 4.26% | 4.26% |
|  | Dyestuff | 21.28% Lanaset Blue 2R | 21.28% Erionyl Blue RL 200% | 21.28% Tectilon Blue 6G | 21.28% Gryfalan Violet RL |
| Part 2 | Water | 88.16% | 88.16% | 88.16% | 88.16% |
|  | Thioglycolic acid | 2.52% | 2.52% | 2.52% | 2.52% |
|  | Sodium sulphite | 2.52% | 2.52% | 2.52% | 2.52% |
|  | 2-amino-2-methyl-1-propanol | 4.28% | 4.28% | 4.28% | 4.28% |
|  | Hydroxyethyl-cellulose | 2.52% | 2.52% | 2.52% | 2.52% |
| Does the hair exhibit any visible fade or colour change after 20 shampoo washes? |  | No | No | No | No |

EXAMPLES 10-13

Hair tresses in the following examples were treated using the same procedure as in example 1.

Percentage values in the table above denote the weight of a given component expressed as a percentage of the total weight of the composition of the part in which it is present.

|  |  | Example 10 | Example 11 | Example 12 | Example 13 |
|---|---|---|---|---|---|
| Starting Hair Colour |  | Bleached blonde | Bleached blonde | Bleached blonde | Bleached blonde |
| Amount of Part 1 |  | 3.2 g | 3.2 g | 3.2 g | 3.2 g |
| Amount of Part 2 |  | 7.9 g | 7.9 g | 7.9 g | 7.9 g |
| Time |  | 15 mins | 15 mins | 15 mins | 15 mins |
| Temperature |  | 40° C. | 40° C. | 40° C. | 40° C. |
| Final Hair Colour |  | Violet | Orange | Red | Orange |
| Part 1 | Urea | 35.46% | 35.46% | 35.46% | 35.46% |
|  | Laurylamidopropylbetaine | 3.55% | 3.55% | 3.55% | 3.55% |
|  | Water | 35.46% | 35.46% | 35.46% | 35.46% |
|  | Hydroxyethylcellulose | 4.26% | 4.26% | 4.26% | 4.26% |
|  | Dyestuff | 21.28% Nylosan Violet F-BL 180 | 21.28% Acidol Red 2BE-N | 21.28% Lanasyl Red SG | 21.28% Neolan Red P |
| Part 2 | Water | 88.16% | 88.16% | 88.16% | 88.16% |
|  | Thioglycolic acid | 2.52% | 2.52% | 2.52% | 2.52% |
|  | Sodium sulphite | 2.52% | 2.52% | 2.52% | 2.52% |
|  | 2-amino-2-methyl-1-propanol | 4.28% | 4.28% | 4.28% | 4.28% |
|  | Hydroxyethyl-cellulose | 2.52% | 2.52% | 2.52% | 2.52% |
| Does the hair exhibit any visible fade or colour change after 20 shampoo washes? |  | No | No | No | No |

EXAMPLE 14

A sample of hair having an initial bleached blonde appearance was treated as follows.

| Part 1 | Part 2 |
|---|---|
| 33.11% Urea | 88.16% Water |
| 3.31% Laurylamidopropylbetaine | 2.52% Thioglycolic acid |
| 33.11% Water | 2.52% Sodium sulphite |
| 3.97% Hydroxyethylcellulose | 4.28% 2-amino-2-methyl-1-propanol |
| 26.49% 2 parts of Telon Black AMF | 2.52% Hydroxyethylcellulose |
| 1 part of Telon BlueAR01 |  |
| 1 part Telon Yellow A2R |  |

Prepare hair treatment mixture, by mixing 3.2 g of part 1 and 7.9 g of Part 2.

Brush mixture into hair and leave at 40° C. for 15 minutes using a liquor ratio of 2.5:1 (2.5 g of preparation mixture:1 g hair tress).

Rinse with warm water.

Massage an after-treatment solution of 30 g/l hydrogen peroxide soln (36%) using same liquor ratio as above.

Rinse with water

Apply L'Oreal Elvive re-Nutrition® conditioner to the hair and leave for 5 minutes Rinse with water Dry as required The resulting hair was a black colour that was found to exhibit no visible fade or colour change after 20 shampoo washes.

EXAMPLES 15-17

Hair tresses in the following examples were treated using the same procedure as in example 14.

|  |  | Example 15 | Example 16 | Example 17 |
|---|---|---|---|---|
| Starting Hair Colour |  | bleached blonde | bleached blonde | bleached blonde |
| Amount of Part 1 |  | 3.2 g | 3.2 g | 3.2 g |
| Amount of Part 2 |  | 7.9 g | 7.9 g | 7.9 g |
| Time |  | 15 mins | 15 mins | 15 mins |
| Temperature |  | 40° C. | 40° C. | 40° C. |
| Final Hair Colour |  | Dark reddish Brown | orangey red | chestnut |
| Part 1 | Urea | 31.06% | 33.11% | 36.50% |
|  | Laurylamidopropylbetaine | 3.11% | 3.31% | 3.65% |
|  | Water | 31.06% | 33.11% | 36.50% |
|  | Hydroxyethylcellulose | 3.73% | 3.97% | 4.38% |
|  | Dyestuff | 31.06% comprising: 2 pts Telon Black AMF 1 pt Telon Blue AR01 1 pt Telon Yellow A2R 1 pt Telon Red A2R | 26.49% comprising: 1.5 pts Telon Red A2R 1.5 pts Telon Yellow A2R 1 pt Telon Yellow M-5GL | 18.98% comprising: 0.6 pts Telon Black AMF 1.5 pt Telon Yellow A2R 0.5 pt Telon Red A2R |
| Part 2 | Water | 88.16% | 88.16% | 88.16% |
|  | Thioglycolic acid | 2.52% | 2.52% | 2.52% |
|  | Sodium sulphite | 2.52% | 2.52% | 2.52% |
|  | 2-amino-2-methyl-1-propanol | 4.28% | 4.28% | 4.28% |
| After treatment 1 |  | $H_2O_2$ 30 g/L (36% soln) | $H_2O_2$ 30 g/L (36% soln) | $H_2O_2$ 30 g/L (36% soln) |
| After treatment 2 |  | L'Oreal Elvive Re-Nutrition (RTM) conditioner | L'Oreal Elvive Re-Nutrition (RTM) conditioner | L'Oreal Elvive Re-Nutrition (RTM) conditioner |
| Does the hair exhibit any visible fade or colour change after 20 shampoo washes? |  | No | No | No |

EXAMPLE 18

A sample of hair having an initial medium brown appearance was treated as follows.

| Part 1 |  | Part 2 |  |
|---|---|---|---|
| 100% | Ammonium carbonate | 97.60% | $H_2O_2$ (9% Soln) |
|  |  | 1.00% | Laurylamidopropylbetaine |
|  |  | 1.40% | Aculyn 22 |

Percentage values in the table above denote the weight of a given component expressed as a percentage of the total weight of the composition of the part in which it is present.

Prepare hair treatment mixture, by mixing 2.0 g of Part 1 and 11.0 g of Part 2.

Brush mixture into hair and leave at 30° C. for 20 minutes using a liquor ratio of 2.5:1 (2.5 g of preparation mixture:1 g hair tress).

Rinse with cold or warm water.

Dry hair

The resulting hair was a bleached blond colour with little or no damage. This hair was then treated as follows:

| Part 1 |  | Part 2 |  |
|---|---|---|---|
| 35.46% | Urea | 75.76% | Water |
| 3.55% | Laurylamidopropylbetaine | 2.16% | Thioglycolic acid |
| 35.46% | Water | 2.16% | Sodium sulphite |
| 4.26% | Hydroxyethylcellulose | 3.68% | 2-amino-2-methyl-1-propanol |
| 21.28% | Telon Navy AMF | 16.23% | Aculyn 28 |

Percentage values in the table above denote the weight of a given component expressed as a percentage of the total weight of the composition of the part in which it is present.

Prepare hair treatment mixture, by mixing 3.2 g of part 1 and 7.9 g of Part 2.

Brush mixture into hair and leave at 40° C. for 20 minutes using a liquor ratio of 2.5:1 (2.5 g of preparation mixture:1 g hair tress).

Rinse with warm water.

Massage an after-treatment solution of 30 g/l hydrogen peroxide soln (36%) using same liquor ratio as above.

Rinse with water

Apply L'Oreal Elvive Re-Nutrition® conditioner to the hair and leave for 5 minutes Rinse with water Dry as required The resulting hair was Navy blue colour that was found to exhibit no visible fade or colour change after 20 shampoo washes. This hair was then treated as follows:

| Part 1 |  | Part 2 |  |
|---|---|---|---|
| 50% | Urea | 92.86% | Water |
| 25% | Thiourea dioxide | 5.84% | 2-amino-2-methyl-1-propanol |
| 25% | Zinc acetate | 1.08% | Laurylamidopropylbetaine |
|  |  | 0.22% | Hydroxyethylcellulose |

Percentage values in the table above denote the weight of a given component expressed as a percentage of the total weight of the composition of the part in which it is present.

Prepare hair treatment mixture, by mixing 2.0 g of part 1 and 9.3 g of Part 2.

Brush mixture into hair and leave at 45° C. for 30 minutes using a liquor ratio of 2.5:1 (2.5 g of preparation mixture:1 g hair tress).

Rinse with warm water.

Dry as required

The resulting hair was a blonde colour with no hint of the previous colour and with little or no damage.

The invention claimed is:

1. A method of colouring a material, the method comprising:
    applying to the material a coloring composition comprising a sulphur-containing nucleophile and
    a dye compound selected from a group of dye classes consisting of: direct dyes, acid leveling dyes, and acid milling dyes,
    wherein the coloring composition comprises from 0.1 wt % to 4.0 wt % of one or more thiols, at least 2 wt % urea, and at least 60 wt % water, and wherein the coloring composition has a pH between 9.0 and 10.5.

2. A colouring composition comprising a sulphur-containing, from 0.1 to 15 wt % of one or more thiols and a dye compound selected from a group of dye classes consisting of: direct dyes, acid leveling dyes, and acid milling dyes.

3. A colouring composition according to claim 2 wherein the sulphur containing nucleophile comprises thioglycolic acid, sodium sulfite or a mixture thereof.

4. A colouring composition according to claim 2 which comprises from 0.1 to 15 wt % of one or more sulfite containing species.

5. A colouring composition according to claim 2 which further comprises urea.

6. A method according to claim 1, wherein the material is human hair.

7. The colouring composition of claim 2, wherein the coloring composition comprises between 0.1 wt % and 4.0 wt % of one or more thiols, at least 2 wt % urea, at least 60 wt % water, and wherein the coloring composition has a pH between 9.0 and 10.5.

* * * * *